United States Patent [19]
Butaric et al.

[11] Patent Number: 6,033,380
[45] Date of Patent: Mar. 7, 2000

[54] SIX-PLEATED CATHETER BALLOON AND DEVICE FOR FORMING SAME

[75] Inventors: Frank Butaric, Pembroke Pines; Mario Rivas, Miami, both of Fla.

[73] Assignee: Cordis Corporation, Miami, Fla.

[21] Appl. No.: 09/023,590

[22] Filed: Feb. 13, 1998

[51] Int. Cl.[7] .................................................. A61M 29/00
[52] U.S. Cl. ............................................ 604/96; 606/194
[58] Field of Search ..................... 604/96–102; 606/192, 606/194

[56] References Cited

U.S. PATENT DOCUMENTS

| | | |
|---|---|---|
| 3,012,274 | 12/1961 | Levy . |
| 4,141,364 | 2/1979 | Schultze ..................................... 604/96 |
| 4,941,877 | 7/1990 | Montano, Jr. ............................. 604/96 |
| 5,015,231 | 5/1991 | Keith et al. . |
| 5,037,392 | 8/1991 | Hillstead . |
| 5,087,246 | 2/1992 | Smith . |
| 5,147,302 | 9/1992 | Euteneuer et al. . |
| 5,209,799 | 5/1993 | Vigil . |
| 5,250,070 | 10/1993 | Parodi ..................................... 604/194 |
| 5,295,995 | 3/1994 | Kleiman ................................... 606/194 |
| 5,342,307 | 8/1994 | Euteneuer et al. . |
| 5,350,361 | 9/1994 | Tsukashima et al. . |
| 5,456,666 | 10/1995 | Campbell et al. . |
| 5,718,684 | 2/1998 | Gupta ......................................... 604/96 |
| 5,792,172 | 8/1998 | Fischell et al. .......................... 606/198 |
| 5,853,389 | 12/1998 | Hijlkema .................................. 604/96 |
| 5,868,776 | 2/1999 | Wright ..................................... 606/194 |

FOREIGN PATENT DOCUMENTS

| | | |
|---|---|---|
| 56-156904 | 12/1981 | Japan . |
| 59-38047 | 3/1984 | Japan . |

Primary Examiner—John D. Yasko
Assistant Examiner—Deborah Blyveis
Attorney, Agent, or Firm—Cook, Alex, McFarron, Manzo, Cummings & Mehler, Ltd.

[57] ABSTRACT

A catheter balloon for use in dilation procedures, such as angioplasty, has multiple pleats formed therein, preferably six such pleats, that may be folded, or wrapped, circumferentially around the catheter to provide a minimized outer diameter when the balloon is deflated. The balloon pleats form six wings in the balloon and each of the balloon wings has a length such that it overlaps a portion of an adjoining wing and each wing extends about one-quarter of the circumference of the catheter shaft. A device for forming such folds in a balloon includes a forming chamber and a plurality of forming elements radially disposed around the balloon.

15 Claims, 6 Drawing Sheets

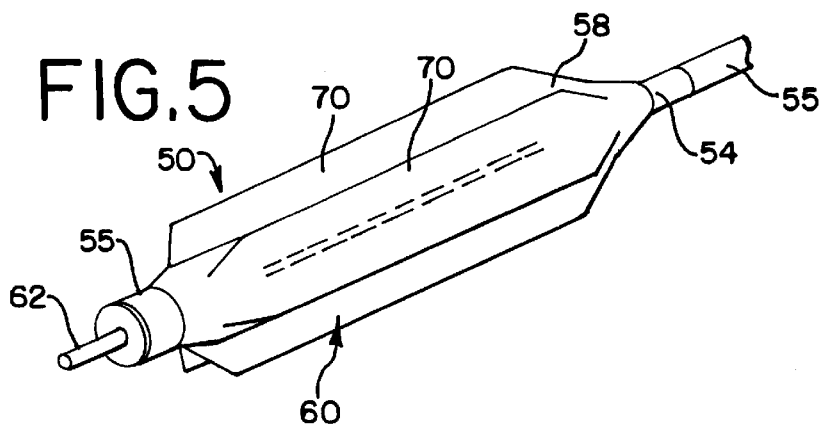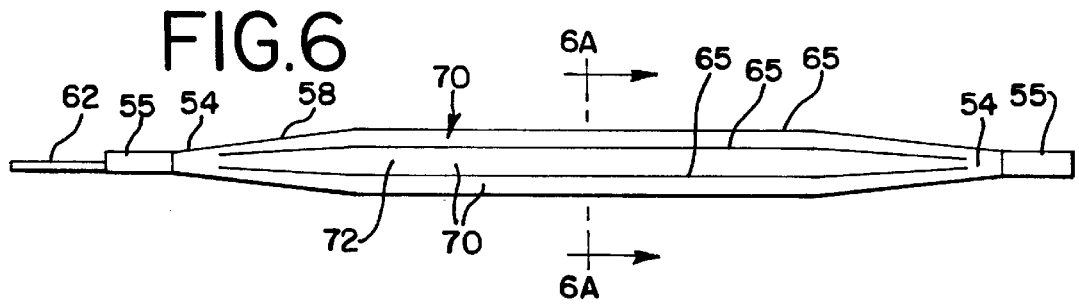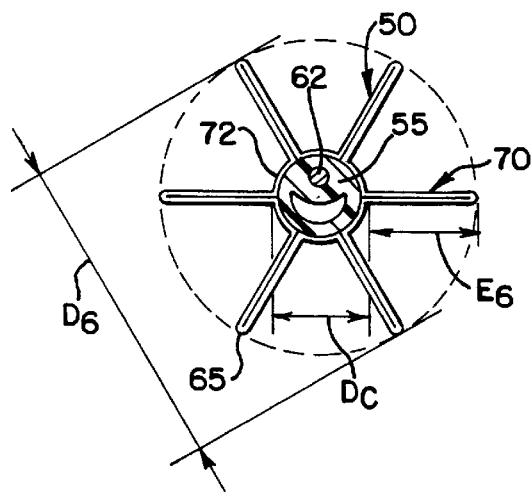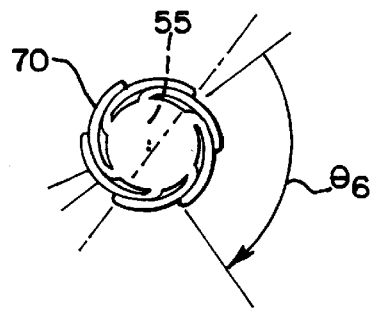

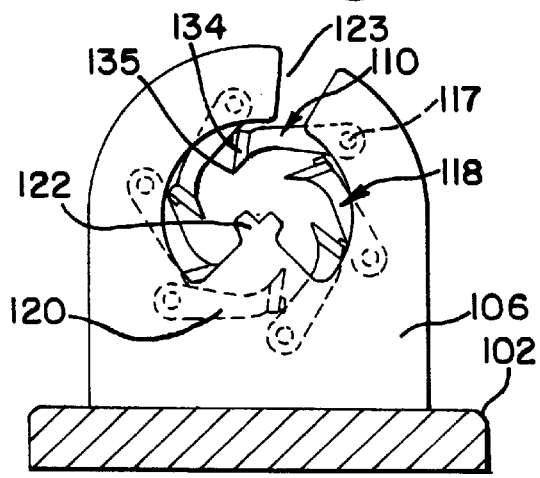
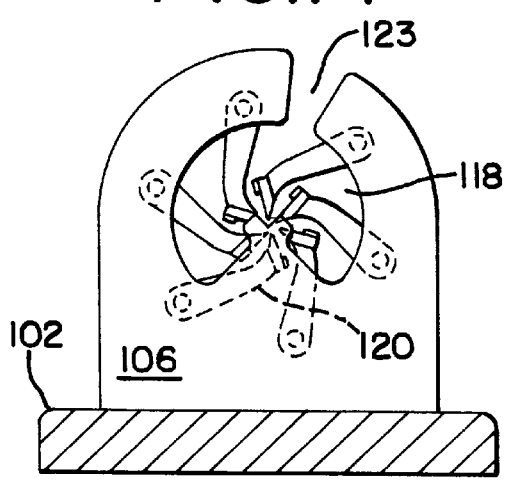
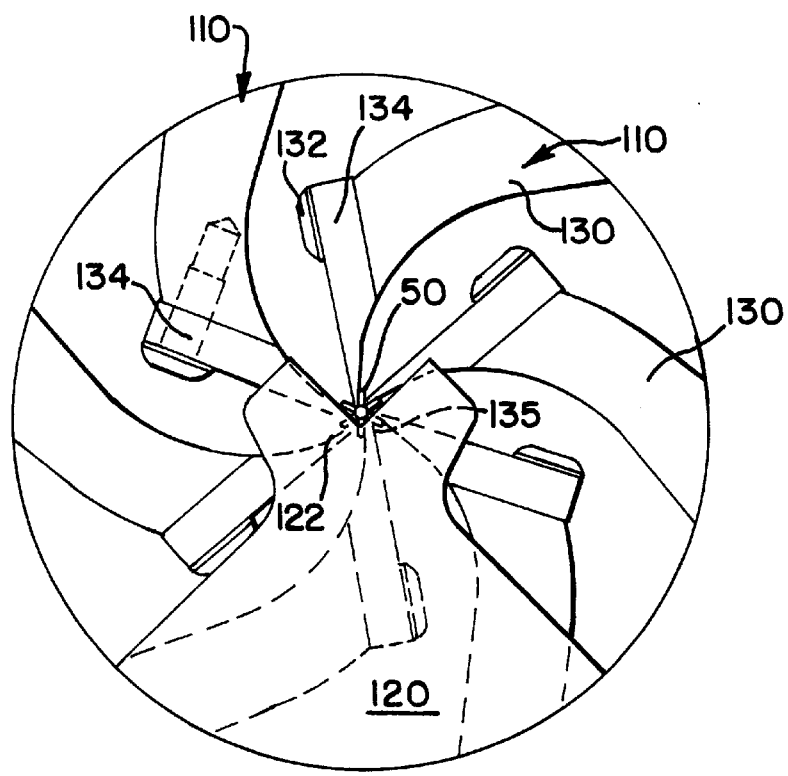

SIX-PLEATED CATHETER BALLOON AND DEVICE FOR FORMING SAME

BACKGROUND OF THE INVENTION

The present invention relates generally to the use and preparation of balloon catheters for angioplasty and other surgical procedures and more specifically, to a multiple pleated balloon and a device for forming multiple pleats in such balloons.

The use of angioplasty to relieve blockages, or occlusions, of blood vessels has increased significantly in recent years. Angioplasty typically involves the insertion of an inflatable balloon into an occluded blood vessel and positioning the balloon at the occlusion. The balloon is then rapidly inflated and deflated in order to expand the occlusion and restore the blood vessel to its original, workable size.

Angioplasty catheters which are used for these procedures typically include a guidewire, a balloon catheter having a guide lumen which receives the guidewire, an inflation lumen extending to the distal end of the catheter and an inflatable balloon positioned at the distal end of a catheter over an opening of the inflation lumen. The balloons used with such catheters typically have an inflatable body portion disposed between two leg portions. The leg portions have a diameter which may be slightly less than the diameter of the catheter at its distal end in order to provide a tight seal which permits inflation and deflation of the balloon. The balloon body portion may have a diameter greater than that of the leg portions and the catheter shaft. Typically, this diameter corresponds to the actual diameter of the balloon when inflated, particularly when a non-expandable material is used for construction of the balloon.

The inflated diameter of angioplasty balloons may range anywhere from between 1.5 to 5.0 mm, while the diameter the catheter at its distal end is in the order of 1.0 mm. The excess balloon material is rolled when deflated upon the catheter distal end portion to facilitate insertion of the balloon into the blood vessel. When so prepared, the balloon will not impinge upon the walls of the blood vessel as it is being positioned within the blood vessel at the site of the occlusion. This balloon preparation is usually accomplished by manually rolling the body of the balloon onto the catheter shaft. Because of the very small dimensions of these balloons, it is difficult and time consuming to ensure that the balloon is accurately and preferably uniformly folded upon itself.

When such balloons are rolled upon their supporting catheters with only one or two folds, the deployment of the balloon during inflation may not occur in a uniform manner, leading to problems in opening the occlusion in the vessel. Additionally, in clearing the occlusion the balloon typically undergoes rapid inflation and deflation. In balloons having one or two folds, when the balloon is deflated, the folds may be too large to permit the balloon to pass rearwardly through the occlusions.

U.S. patent application Ser. No. 589,766, assigned to the assignee of the present invention, describes the use of a multiple part balloon press for forming folds in an angioplasty balloon in which the balloon press has two balloon-contacting members with a central channel extending along at least one of the balloon contacting members. Although this device is effective for forming two opposing folds in the catheter balloon, The press must be used repeatedly at different angular orientations in order to form more than two folds in the catheter balloon. It may be difficult to utilize this device to form more than two uniform folds in the catheter balloon. Using the device in this manner may lead to undesirable inaccurate forming of folds which may affect the inflation properties of the balloon.

U.S. Pat. No. 5,342,307, issued Aug. 30, 1994 and U.S. Pat No. 5,350,361, issued Sep. 27, 1994 describe dilation balloons with three folds. Although the balloons therein have three folds, the diameter of the balloon in an uninflated state is still relatively large due to the three folds, and a physician may have some difficultly in pulling the distal end of the catheter rearwardly through a lesion in the blood vessel. Additionally, in balloons having three such folds, the folds define three "wings" of the balloon which must be wrapped around the catheter shaft to facilitate removal of the catheter and balloon from the blood vessel. The length of these wings are such that they require the catheter distal end to be rotated for almost one revolution to complete the wrapping of the balloon wings or folds upon the catheter. This increases the complexity of the dilation procedure. To applicants' belief, there are no dilation balloons in the art that utilize more than three folds.

The present invention therefore is directed to a six-pleated catheter angioplasty balloon and a device for forming multiple pleats in such balloons while they are attached to the catheter shaft and which simplifies rolling or folding of the balloon body onto the catheter shaft. The present invention therefore ensures that the proper folded configuration of the balloon on the catheter distal end portion is achieved prior to insertion of the balloon catheter into the blood vessel.

SUMMARY OF THE INVENTION

Accordingly, it is an object of the present invention to provide a pleating device for forming folds in angioplasty balloons which is compact and which reliably forms at least six folds, or pleats in a dilation balloon, typically an angioplasty balloon in a uniform manner that facilitates wrapping of the balloon around the catheter shaft.

Another object of the present invention is to provide a multi-pleated balloon for an angioplasty catheter in which the balloon has multiple pleats, preferably six pleats, uniformly spaced around the circumference of the balloon. The pleats are formed in the balloon in a device while the balloon is inflated. This device includes a plurality of balloon-contacting members that simultaneously impinge upon the inflated balloon at six different, equally spaced locations around the balloon perimeter so that the resulting balloon folds or pleats are uniform.

Yet another object of the present invention is to provide a balloon forming device suitable for use with percutaneous transluminal coronary angioplasty (PTCA) catheters and other dilation catheters, the device comprising a balloon-supporting jig having multiple balloon-contacting members disposed thereon in equal locations around the circumferential perimeter of the balloon, the balloon-contacting members being biased into an open position to permit entrance of an inflated balloon therein and operable into a closed position wherein the balloon-contacting members extend radially inwardly into contact with the balloon, to thereby form a plurality of folds in the balloon body at predetermined intervals around the circumference of the balloon.

Still another object of the present invention is to provide a method for forming six pleats in angioplasty balloon secured to and around the distal end portion of an angioplasty catheter, wherein the method comprises the steps of inflating the balloon to a distended state, providing a balloon forming assembly with a plurality of balloon-contacting members disposed thereon at equal intervals around the exterior circumference of the balloon, inflating the balloon and placing the inflated balloon into the assembly between opposing balloon-engagement surfaces of the balloon-contacting members, drawing the confronting balloon-engagement surfaces into contact with the balloon and deflating the balloon during such contact to thereby form at multiple folds in the balloon body portion.

Yet another object of the present invention is to provide a dilation balloon for a dilation catheter having six or more pleats formed in a body portion of the balloon, the pleats defining wings in the balloon that may be wrapped around the shaft of the dilation catheter, the wings of the balloon having a length that extends around the catheter shaft that is less than one-half of the catheter shaft circumference.

These and other objects, features and advantages of the present invention will be clearly understood through a consideration of the following detailed description.

BRIEF DESCRIPTION OF THE DRAWINGS

In the course of the following detailed description, reference will be frequently made to the accompanying drawings in which:

FIG. 5 is a perspective view of the balloon catheter of FIG. 4 with the balloon illustrated in a partially deflated state to illustrate the pleats of the balloon;

FIG. 6 is a plan view of the catheter balloon of FIG. 5;

FIG. 6A is a cross-sectional view of the catheter balloon of FIG. 6 taken along lines A—A thereof and illustrating the pleats of the balloon;

FIG. 6B is the same view of as FIG. 6A with the catheter removed for clarity and with the balloon pleats wrapped around the catheter;

FIG. 13 is an end view of the left end of the balloon-forming device of FIG. 13 illustrating the balloon support and the balloon-contacting members in an open arrangement;

FIG. 14 is the same view as FIG. 13 but illustrating the balloon-contacting members in a closed position; and, FIG. 15 is an enlarged detail view of the balloon and the balloon-contacting members of FIG. 13.

DETAILED DESCRIPTION OF THE PREFERRED EMBODIMENTS

Figure 1:
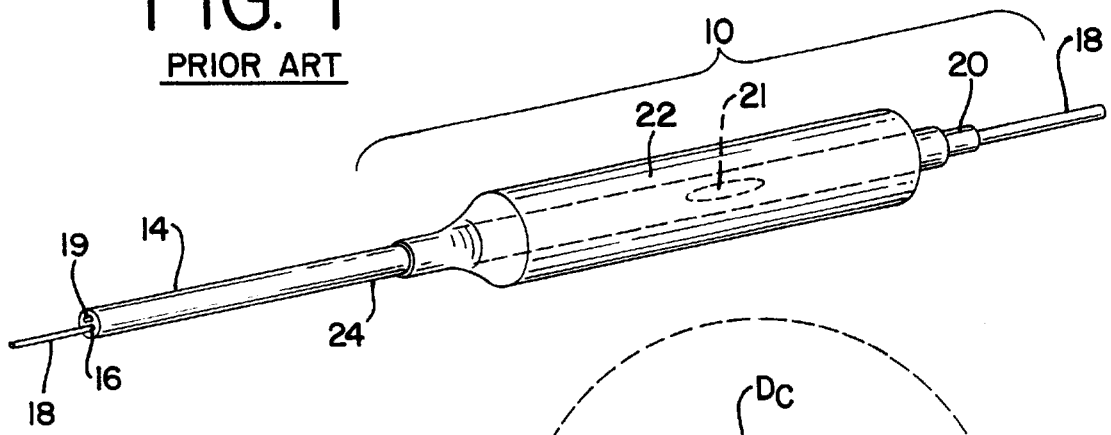
FIG. 1 is a perspective view of a conventional balloon catheter illustrating the distal end portion thereof.

A conventional dilation balloon catheter assembly is illustrated generally at 10 in FIG. 1. Such balloon catheter assemblies 10 are commonly used in angioplasty, or other dilation procedures for clearing partially or substantially blocked blood vessels. As is known in the art, the catheter assembly 10 is typically inserted into a blood vessel and moved through the vessel to the site of the blockage where it is inflated and deflated to compress and reduce the blockage.

Figure 2:
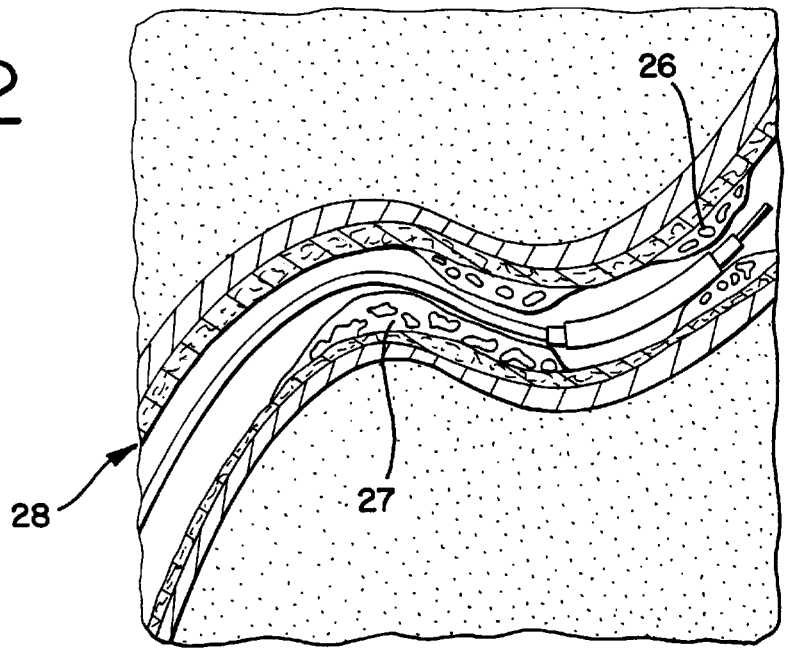
FIG. 2 is a cross-sectional view of a blood vessel with two occlusions and with a balloon catheter inserted therein.

The catheter assembly 10 is conventional in construction and is seen to include an elongated catheter 14 with a guidewire lumen 16 extending longitudinally therethrough. A guidewire 18, which is received within the lumen 16, permits positioning of the distal end 20 of the catheter assembly 10 within an occlusion 26 of a blood vessel 28 as illustrated in FIG. 2.

Figure 1A:
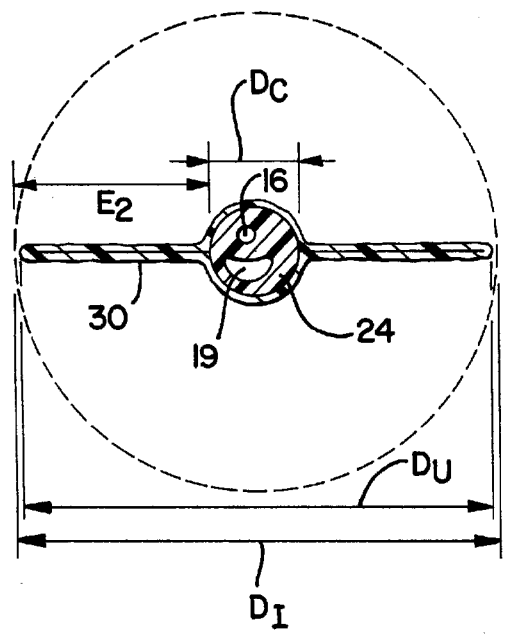
FIG. 1A is a diagrammatic view illustrating the extent of the balloon of the catheter of FIG. 1 in an inflated and uninflated state.

An inflation lumen 19 also extends through the catheter 14 and terminates in an inflation opening or port 21 shown in phantom in FIG. 1. An inflatable dilation balloon 22 is attached to the catheter shaft 24 at the distal end 20 and overlies the inflation port 21 thereof. As illustrated in FIG. 1A, the balloon 22 when inflated, has an inflated diameter $D_I$. This inflation is done under pressure of an inflation media pumped through the inflation lumen 19 and into the balloon 22 through the inflation port 20. When inflated, the balloon will press outwardly against the occlusion 26 and achieve its inflated diameter taking a configuration such as that represented by the dashed circle of FIG. 1A.

The balloon 22 is then deflated by withdrawing the inflation media out of the inflation port 21 and the balloon 22 will collapse in the general manner as illustrated in FIG. 1A. At this stage, the balloon 22 may be considered as having a deflated diameter $D_U$, which most times will be slightly less than $D_I$. This deflation in effect causes the formation of wings, or folds, 30 that extend out from the catheter. These wings 30, due to their extent $E_2$, (the distance from an end of the wing 30 to the catheter shaft 24,) may catch or hang up on a second occlusion 27 in the blood vessel. One solution to this is to rotate the catheter either clockwise or counterclockwise in the hope that the wings 30 will wrap themselves around the catheter shaft and adopt a low profile.

Figure 3:
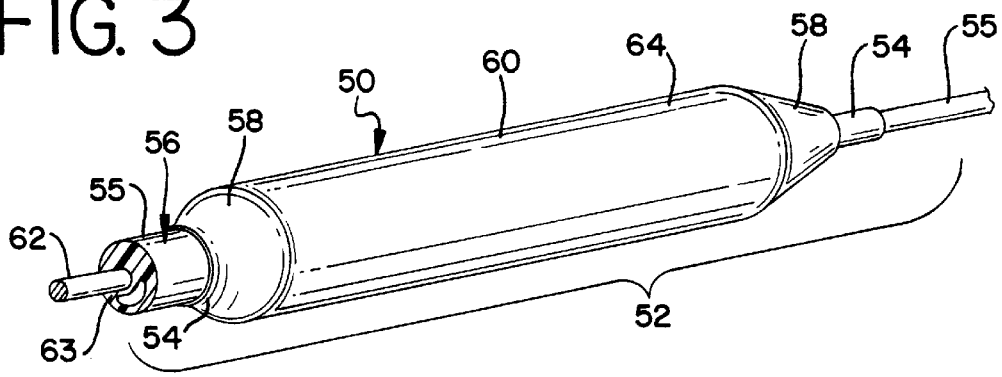
FIG. 3 is a perspective view of the distal end of a balloon catheter constructed in accordance with the principles of the present invention, with the balloon illustrated in an inflated state.

The present invention is directed to a balloon structure that overcomes the aforementioned shortcomings. FIG. 3 illustrates a dilation balloon 50 constructed in accordance with the principles of the present invention. The balloon 50 is depicted as part of an overall catheter assembly 52. The balloon 50 is shown inflated in FIGS. 3, 4 & 4A and has an inflated diameter of $D_1$. The balloon 50 has two opposing end or leg portions 54 that secure the balloon 50 to the catheter shaft 55. These leg portions 54 may have a diameter that is less than that of the catheter 56 to firmly engage the catheter 56 and to provide a seal thereagainst during inflation and deflation of the balloon 50. These leg portions 54 may also be sealed to the catheter in other conventional manners.

The balloon 50 also may have as illustrated, two annular transition portions 58 that are disposed adjacent the balloon leg portions 54 and ramp, or extend, up to a body portion 60 of the balloon which has a working length L that extends between the transition portions 58. The balloon 50 is positioned by a physician within a blood vessel 24 in the manner illustrated in FIG. 2 by the use of a guide wire 62 that extends through a guidewire lumen 63 in the catheter shaft 55.

As is known in the art, the balloon 50 may be formed form a variety of materials, such as nylon, PET (polyethylene terephthalate) which has relatively no expansion characteristics to a polyamide homopolymer, copolymer or blend of polyamide homopolymer and copolymer, which has highly controlled expansion characteristics. No matter what type of material is used for the balloon 50, when the balloon 50 has no such pleats, the body portion 60 of the balloon 50 extends outwardly from the catheter shaft 55 of the catheter assembly 52 when the balloon 50 is in either an inflated or uninflated state. The diameters $D_1$ of the balloon body portions 60 may vary from about 1.5 to about 5.0 mm while the diameter of the catheter is in the order of about 1 mm. Thus, the extension of the balloon 50 in an unpleated condition will therefore be somewhat large compared to the diameter of the catheter shaft 55, anywhere from about 150% to about 500% thereof.

Thus, the balloon body portion 60, inasmuch as it extends from the catheter shaft 55, may prove to be a temporary impediment to the insertion of the balloon catheter 52 into the blood vessel 28 because it may flap around and catch on portions or walls of the blood vessel 28 or on the occlusions 26, 27. In order to prevent this problem, the body portion 60 of the balloon 50 is typically wrapped around the catheter shaft 55 prior to insertion or retraction of the catheter assembly 52 into the blood vessel 28.

Figure 4:
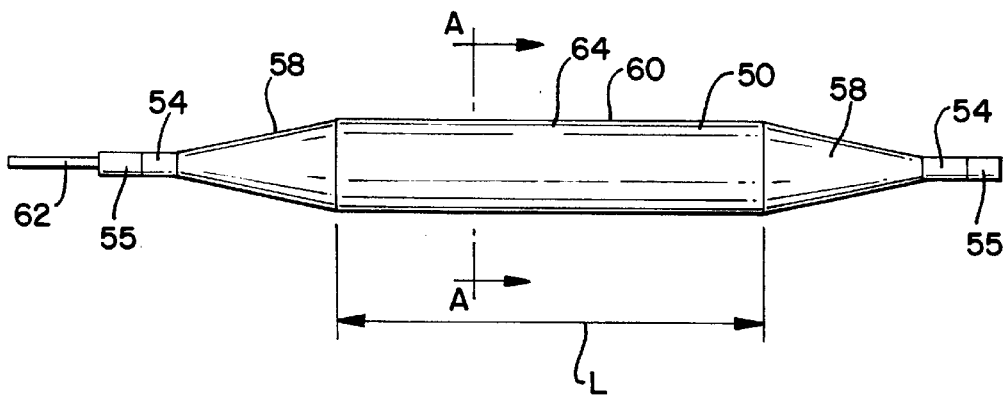
FIG. 4 is a plan view of the catheter balloon of FIG. 3.
Figure 4A:
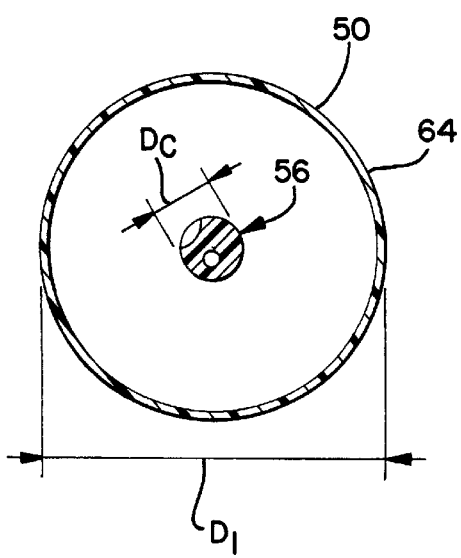
FIG. 4A is a cross-sectional view of the catheter balloon of FIG. 4 taken along lines A—A thereof.

In an important aspect of the present invention and as illustrated in FIGS. 4–6, the balloons 50 of the invention are formed with multiple folds or pleats 70, with six such pleats 70 being illustrated. These pleats 70 occur primarily in the body portion 60 of the balloon 50 and have a length, or extension, $E_6$ that, when formed cooperatively define an overall uninflated diameter $D_6$ of the balloon 50.

These multiple pleats 70 may be considered as "wings" that when the balloon 50 is uninflated as illustrated in FIG. 6A, extend radially outwardly from the catheter and which serve to reduce the overall uninflated diameter $D_6$ of the balloon 50. The folds 70 are preferably formed at equal intervals (further preferably at about 60°) around the circumference of exterior surface 64 of the balloon body portion 60. The use of six such folds 70 is significant because it significantly reduces the extent that the balloon folds 70 project when the balloon is initially deflated to the form of the FIG. 6A, which may be considered as a primary profile of the balloon when ready for insertion.

Figure 7:
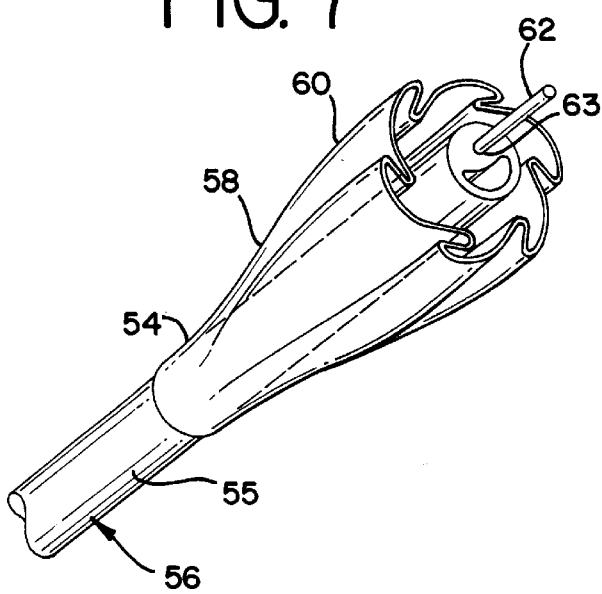
FIG. 7 is a perspective view of the balloon catheter of FIG. 5, partially in section illustrating the manner in which the deflated balloon may be folded around the catheter and its relationship to the catheter shaft.

These pleats 70 have an extent $E_6$ that equals the distance from the catheter shaft 55 to the pleat end 65. The six pleats 70 reduce the immediate deflated profile of the balloon 50 as illustrated in FIG. 5 so that the projecting wing extent $E_6$ is significantly small, approaching the order of about approximately 125% of the diameter $D_c$ of the catheter shaft 55. In between the pleats or folds 70, troughs 72 exist to separate the folds 70 form one another. When so pleated, the pleats 70 may be wrapped upon the catheter shaft 55 in the manner illustrated in FIGS. 6B & 7, wherein each pleat 70 will overlie an adjoining pleat to some small extent. The manner in which the balloon folds 70 appear after such wrapping is generally shown in FIG. 6B. FIG. 7 may be considered as having a secondary profile of the balloon when it has been deflated after inflation and when it is ready for retraction into the guiding catheter.

Figure 8:
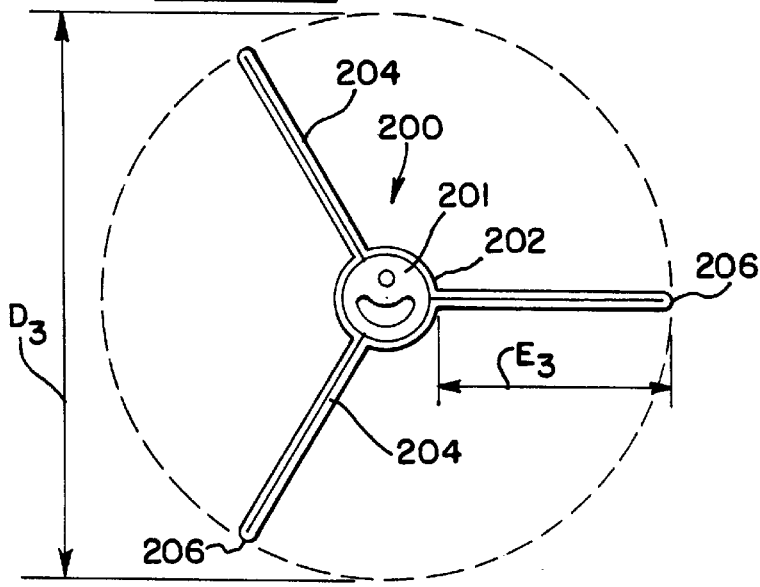
FIG. 8 is a cross-sectional view of a three pleated or tri-fold balloon catheter with the balloon deflated.
Figure 8A:
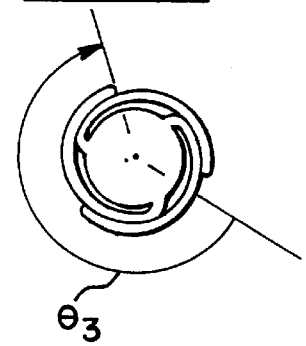
FIG. 8A is the same view as FIG. 8 with the balloon pleats folded around the catheter shaft.

FIG. 8 illustrates, in cross-section, a balloon catheter assembly 200 in which the dilation balloon 202 thereof has three folds or pleats 204 when the balloon 202 is in the uninflated condition illustrated. The balloon 202 is of conventional size, that is, the inflated diameter thereof is about 0.16 inches (4.0 millimeters). The three pleats 204 cooperatively define an uninflated diameter $D_3$ of the balloon 202. Each balloon pleat 204 has an extent $E_3$ that runs from the catheter shaft 201 to a respective end tip 206. Such balloons 202 are known in the art as described above. This balloon fold arrangement leads to certain shortcomings. For example, the uninflated and unwrapped diameter $D_3$ of such a tri-fold balloon 202 having a balloon thickness of about 0.001 inches (0.02 millimeters) will be approximately 0.155 inches (3.93 millimeters). The extent $E_3$ of each pleat 204 is sufficiently long that it extends rather long circumferentially around the catheter 201. This extent is represented in FIG. 8 as angle $\theta_3$ that extends around the circumference of the catheter 201 for a range of between approximately 220° and approximately 270°.

In the balloons 50 of the present invention, the increased number of pleats 70 significantly reduces the uninflated and unwrapped diameter $D_6$ of the balloon 50. For example, in a six pleated balloon having an inflated diameter of about 0.16 inches (4.0 millimeters) and a balloon wall thickness of about 0.001 inches (0.02 millimeters), will have a deflated diameter of approximately 0.090 inches (2.28 millimeters). The increased number of pleats 70 reduces the uninflated diameter $D_6$ of the balloons of the present invention by almost 43% as compared to the uninflated and unwrapped diameter (0.155 inches and 3.93 millimeters) of the conventional tri-fold balloon exemplified in FIG. 8. The extent $E_6$ of each pleat 70 is significantly reduced and extends circumferentially when wrapped around the catheter shaft 55 through a range of angles $\theta_6$ between approximately 70° and 90° and preferably less than 90°.

This reduced distance is significant to the operation of the balloon catheter assembly because it reduces the effort to wrap a deflated balloon 50 onto the catheter shaft 55 by the operating physician. Such a catheter need only be rotated about one-quarter turn to wrap the balloon, while a tri-fold balloon catheter would have to be rotated about three-quarters of a turn. The wrapping with the balloons of the present invention should require no more than a simple wrist rotation. Balloons having diameters of about between 3.5 and about 5.0 millimeters will benefit from such pleating.

Figure 9:
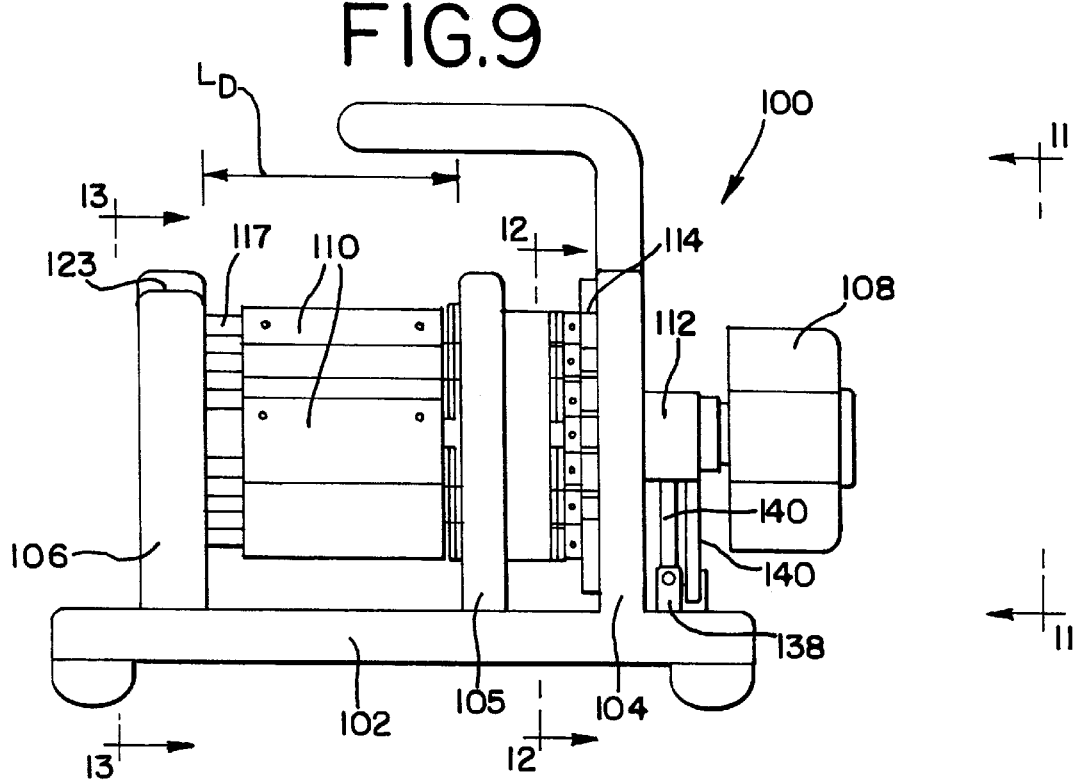
FIG. 9 is an elevational view of a device suitable for forming the pleats in the balloons of the balloon catheters of FIG. 3.
Figure 12:
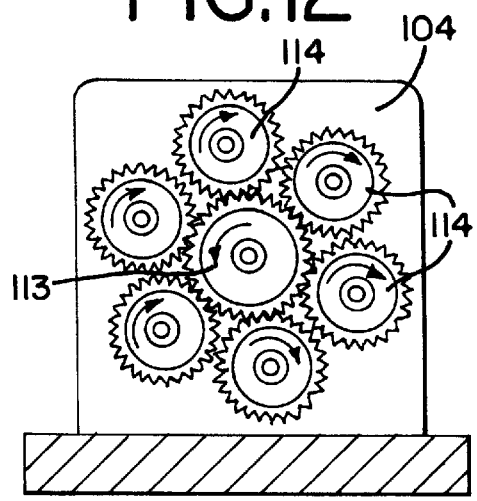
FIG. 12 is a cross-sectional view of the balloon forming device of FIG. 9 taken along lines 12—12 thereof and illustrating the gear assembly that drives the balloon-contacting members.

FIG. 9 illustrates a device 100 for forming six or more pleats 70 in the balloons 50 of the present invention. The device 100 is small and hand-operated. It includes a mounting base 102 that supports three vertical columns 104, 105 and 106 that support the balloon forming components of the device 100. A manually manipulatable knob 108 is provided at one end thereof and is rotatably supported in an opening (not shown) in the first column 104. This knob is operatively connected to a plurality of balloon-contacting members 110 (FIG. 12) that are rotatably disposed on the first column 102. A slip clutch mechanism 112 is interposed between the knob 108 and the first column 102 and the clutch 112, in turn, governs the speed at which a drive gear 113 rotates during operation. This drive gear 113 is meshed with a plurality of driven gears 114, one such driven gear 114 being associated with a single one of balloon-contacting members 110.

The balloon-contacting members 110 extend axially between the second and third columns 105, 106 and have a working length $L_D$ that is at least equal to and preferably slightly greater than the working length L of the balloon 50. Lengths of about 1 inch (2.3 or so centimeters) or so have provided desirable results. The balloon-contacting members 110 are rotatably supported in their extent by a series of support rods or pins 117 that also extend in the gap between the first and second columns 105, 106 through the associated gears 113 and 114. The third column 106 has a central opening 118 formed therein around which the balloon-contacting members 110 are positioned. This opening includes a balloon support member 120 with a support cradle 122 formed at its end and positioned in the center of the opening 118 thereof. The column 106 has a slot 123 that communicates with its opening 118 which permits the insertion of a balloon into the opening 118 and the support cradle 122.

Each balloon-contacting member 110 as best illustrated in FIG. 15 may include an elongated base arm member 130 that has an opening 131 formed in one end thereof for engaging one of the driven gears 114. At the other end, the arm member 130 is tapped to receive a series of screws 132 that affix a contact arm 134 that extends generally transverse to the base arm 130. This contact arm 134 may be made from a suitable plastic such as Delrin while the base arm may be formed from a metal, preferably stainless steel. The contact arm 134 includes a blunt contact face 135 at the end thereof that contacts the exterior surface of the balloon 50.

In operation, a balloon catheter 52 is inserted into the device 100 by passing the distal end thereof through the device balloon slot 123 of the third column 106

The gears 113, 114 of the device are chosen to have a ratio such that a small turn of the knob 108 will bring the balloon-contacting arms 134 into contact with an inflated balloon 50. In order to prevent the arms 134 from traveling too far in their balloon-contacting path, the device 100 is preferably equipped with a safety stop mechanism 136. This mechanism 136 is shown in FIGS. 7 and 8 to include a pair of stop blocks 138 affixed to the base 102 which are spaced apart a preselected distance G. Two dowel pins 140 extend radially outwardly from the slip clutch 112 in proximity to the stop blocks 138 and are spaced a predetermined angular distance apart, represented by angle $\theta_B$ in FIG. 11. This angle $\theta_B$ is chosen to correspond to a particular rotation of the device gears 113, 114 and is enough to move the balloon-contacting members 110 from their open arrangement shown in FIG. 10 to their closed arrangement shown in FIG. 11. The stop blocks will prevent over-rotation of the contacting assembly and over-movement of the balloon-contacting members 118.

Figure 10:
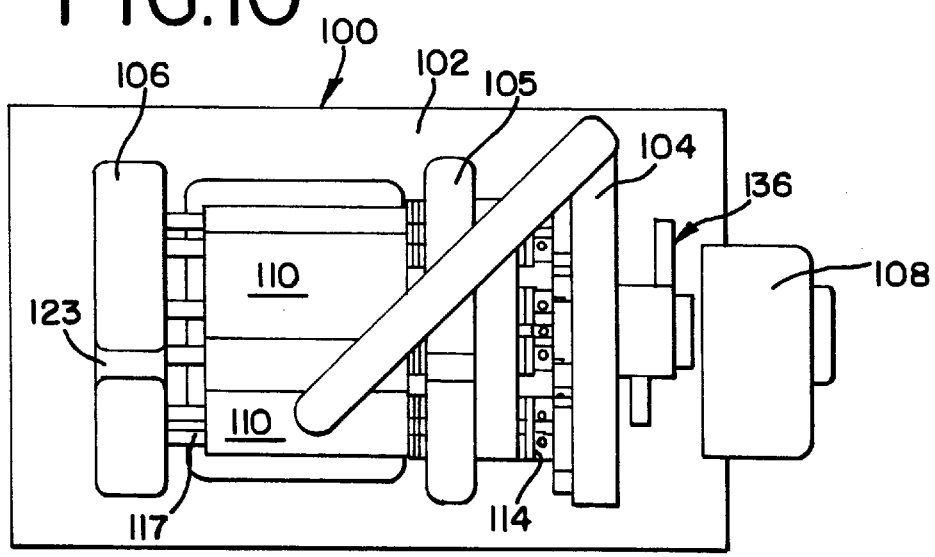
FIG. 10 is a top view of the balloon forming device of FIG. 9.
Figure 11:
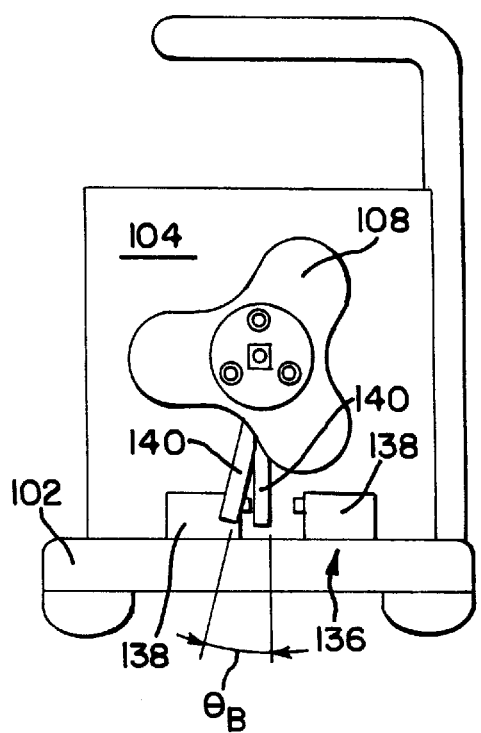
FIG. 11 is an end view of the balloon forming device of FIG. 9.

In operation, the knob 108 is turned to open the balloon-contacting members 110 as shown in FIG. 10. A balloon catheter 52 is placed into the opening 118 of the device and is positioned on the cradle support. The balloon 50 is then inflated (or it may be inflated prior to insertion into the device) and the knob 108 is turned in one direction until one of the dowel pins contacts its corresponding stop block, during which time, the balloon-contacting members are driven in rotation by their associated gears 114 around the rods. During this movement, the balloon-contacting members 110 enter the opening 118 and pivot toward the center thereof and the cradle support. The contact arias 134 of these members 110 impinge upon the exterior surface of the inflated balloon 50. The balloon 50 is thereupon deflated and the contact arms 134 thereby form folds or pleats 70 in the balloon 50 as it deflates.

The increased number of pleats not only facilitates the wrapping of the balloon 50 upon the catheter 55, but also should lead to a more uniform deployment of a stent placed over the balloon 50 in that the pleats will more evenly distribute deployment pressure onto the overlying stent.

While the preferred embodiment of the invention have been shown and described, it will be understood by those skilled in the art the changes or modifications may be made thereto without departing from the true spirit and scope of the invention.

We claim:

1. An improved dilation balloon catheter for use in dilation therapy, wherein the balloon catheter is inserted into a blood vessel of a patient and alternately placed into an inflated condition and a deflated condition within the blood vessel by an operator from a remote location, comprising:

elongated catheter terminating in a distal end portion, the catheter having a shaft of predetermined diameter and a given circumference, said catheter including an inflation lumen extending through said catheter and terminating in an inflation port near said distal end, said catheter further including an inflatable dilation balloon disposed on said catheter shaft near said distal end portion thereof, the balloon having a generally cylindrical balloon body portion with two opposing annular transition portions between said cylindrical body portion and two opposing ends, said cylindrical body portion having a first preselected diameter when said balloon is in said inflated condition, two catheter securement portions adjoining said balloon body portion at said opposing ends thereof, the catheter securement portions having a diameter smaller than that of said balloon body portion at said first preselected diameter, said catheter securement portions being affixed to said catheter shaft on opposite sides of said inflation port, said balloon body portion including six pleats spaced at circumferential intervals around said balloon body portion when said balloon is in said deflated condition, said balloon having a second preselected diameter in said deflated condition that is less than said first preselected diameter, each of said balloon pleats defining corresponding wings of said balloon in said deflated condition, each of said wings extending the full length of the balloon body between said transition portions, each of said wings having an end tip spaced apart from said catheter shaft, said wings further each having a width defined between said wing end tip and said catheter shaft, and said balloon having a blood vessel insertion condition at which said balloon wings are wrapped around said catheter shaft, said balloon wing widths being such that each wing overlaps an adjoining balloon wing when said wings are wrapped around said catheter shaft at said blood vessel insertion condition.

2. The dilation balloon of claim 1, wherein said six balloon pleats are formed at equal circumferential intervals around said balloon body portion.

3. The dilation balloon of claim 2, wherein each of said balloon wing widths are such that when said wings are wrapped around said catheter shaft, said balloon wings each extend only about one-quarter of said catheter shaft circumference.

4. The dilation balloon of claim 2, wherein each of said balloon wings extend around part of said circumference of said catheter shaft when wrapped, each of said balloon wings extending no more than one-half of said catheter shaft circumference.

5. The dilation balloon of claim 4, wherein said balloon has a wall thickness of about 0.001 inches (0.002 millimeters).

6. The dilation balloon of claim 4, wherein said catheter shaft has a diameter of about 0.04 inches (1.0 millimeters), and said catheter balloon first preselected diameter ranges from between about 0.078 inches (2.0 millimeters) to about 0.31 inches (8.0 millimeters).

7. The dilation balloon of claim 4, wherein said balloon is made from nylon.

8. The dilation balloon of claim 4, wherein said balloon is made from polyethylene terephthalate.

9. The dilation balloon of claim 4, wherein said balloon is made from a polyamide homopolymer, copolymer or blend of polyamide homopolymer and copolymer.

10. The dilation balloon of claim 1, wherein said catheter balloon second preselected diameter is about 40% less than said first preselected diameter.

11. An angioplasty balloon for an angioplasty catheter assembly wherein the catheter assembly includes an elongated catheter with a distal end portion and a given circumference, the catheter including a hollow inflation lumen extending through said catheter and terminating near said distal end portion in an inflation opening, the balloon being capable of being inflated and deflated under pressure from an inflation media supplied through said catheter lumen, said balloon comprising:

two leg portions disposed at opposite ends of said balloon which engage said catheter distal end portion, an inflatable body portion intermediate of said balloon leg portions, said balloon body portion having a diameter greater than a diameter of said catheter distal end portion, said balloon further including six pleats formed in at least said balloon body portion, the balloon pleats having a length extending longitudinally along the entirety of said balloon body portion and being spaced at intervals from each other around the circumference of said catheter distal end portion, each of said balloon pleats having a width that extends radially out from said catheter shaft when said balloon is in a deflated condition, said balloon has a blood vessel insertion condition at which said balloon pleats are wrapped circumferentially around said catheter shaft distal end portion, and each said balloon pleat width extends only between about 70° and about 90° around said catheter shaft circumference and overlaps and engages an adjoining balloon pleats when said pleats are at said blood vessel insertion condition.

12. The angioplasty balloon as defined in claim 11, wherein said balloon has an inflated diameter that ranges between about 0.078 inches (2.0 millimeters) to about 0.31 inches (8.0 millimeters).

13. The angioplasty balloon as defined in claim 11, wherein said balloon has an inflated diameter of about 3.5 millimeters.

14. The angioplasty balloon as defined in claim 11, wherein said balloon pleats are formed at equal circumferential intervals around said catheter shaft circumference.

15. The angioplasty balloon as defined in claim 11, wherein said balloon has a diameter in said deflated condition that is at least about 40% less than a diameter of said balloon in an inflated condition.

\* \* \* \* \*

UNITED STATES PATENT AND TRADEMARK OFFICE
CERTIFICATE OF CORRECTION

PATENT NO : 6,033,380
DATED : March 7, 2000
INVENTOR(S) : Frank Butaric and Mario Rivas It is certified that error appears in the above-identified patent and that said Letters Patent are hereby corrected as shown below:

On the Cover Page, under "References Cited, Foreign Patent Documents", please include reference --418,611   9/1925   Germany--.
Col. 1, lines 35-36, "diameter the catheter" should read --diameter of the catheter--; line 64, delete "The" and insert --the--.
Col. 3, line 47, "same view of as" should read --same view as--.
Col. 4, line 4, "FIG. 13 illustrating" should read --FIG. 9 illustrating--.
Col. 5, line 13, delete "form" and insert --from--; line 44, "formed cooperatively" should read --formed, cooperatively--; line 66, delete "form" and insert --from--.
Col. 7, line 34, insert a period --.-- after "column 106"; line 66, delete "arias" and insert --arms--.
Col. 8, line 11, "art the changes" should read --art that changes--; line 20, insert --an-- before "elongated".
Col. 10, line 16, "pleats when said pleats" should read --pleat when said pleats--.

Signed and Sealed this

Seventeenth Day of April, 2001

*Attest:*

NICHOLAS P. GODICI

*Attesting Officer*     Acting Director of the United States Patent and Trademark Office